(12) United States Patent
Suchkov et al.

(10) Patent No.: US 11,849,997 B2
(45) Date of Patent: Dec. 26, 2023

(54) APPARATUS AND METHOD FOR DETERMINING THE REFRACTIVE ERROR OF AN EYE

(71) Applicant: Carl Zeiss Vision International GmbH, Aalen (DE)

(72) Inventors: Nikolai Suchkov, Tübingen (DE); Alexander Leube, Aalen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/181,671

(22) Filed: Mar. 10, 2023

(65) Prior Publication Data

US 2023/0210361 A1 Jul. 6, 2023

Related U.S. Application Data

(63) Continuation of application No. PCT/EP2021/000112, filed on Sep. 24, 2021.

(30) Foreign Application Priority Data

Sep. 24, 2020 (EP) .................... 20 198 056

(51) Int. Cl.
*A61B 3/103* (2006.01)
*A61B 3/00* (2006.01)
*A61B 3/032* (2006.01)
*A61B 3/09* (2006.01)
*A61B 3/14* (2006.01)
*A61B 3/18* (2006.01)

(52) U.S. Cl.
CPC ............ *A61B 3/103* (2013.01); *A61B 3/0025* (2013.01); *A61B 3/032* (2013.01); *A61B 3/09* (2013.01); *A61B 3/14* (2013.01); *A61B 3/18* (2013.01)

(58) Field of Classification Search
CPC ....... A61B 3/103; A61B 3/0025; A61B 3/032; A61B 3/09; A61B 3/14; A61B 3/18
USPC ....................................................... 351/214
See application file for complete search history.

(56) References Cited

U.S. PATENT DOCUMENTS 4,293,198 A 10/1981 Kohayakawa et al.
4,376,573 A * 3/1983 Matsumura ............ A61B 3/103
351/212

(Continued)

FOREIGN PATENT DOCUMENTS

| ES | 482663 | 11/1980 |
|---|---|---|
| WO | 2007033326 A2 | 5/2009 |
| WO | 2013165689 A1 | 11/2013 |

OTHER PUBLICATIONS

G. Colicchia et al., "Measuring aberration of the eye with wavefront technology," Physics Education, vol. 41, No. 4, pp. 307-310, Jul. 2006.

(Continued)

*Primary Examiner* — Mohammed A Hasan
(74) *Attorney, Agent, or Firm* — Tautz & Schuhmacher LLC; Georg M. Hasselmann (57) ABSTRACT

Apparatuses or methods for determining a refractive error of an eye are disclosed. An intensity of light coming from an eye is measured, using a detector device, through at least two or at least three different apertures of the aperture device. The refractive error is then calculated based on the measured intensities.

18 Claims, 4 Drawing Sheets

(56) References Cited

U.S. PATENT DOCUMENTS

| | | | |
|---|---|---|---|
| 4,820,037 A * | 4/1989 | Kohayakawa | A61B 3/103 351/211 |
| 2007/0222948 A1* | 9/2007 | Dai | A61F 9/00804 351/212 |
| 2008/0278683 A1* | 11/2008 | Su | A61B 3/14 351/205 |
| 2010/0110379 A1* | 5/2010 | Zhou | A61B 3/14 351/205 |
| 2015/0131050 A1* | 5/2015 | Bublitz | A61B 3/12 351/246 |
| 2016/0205298 A1* | 7/2016 | Zhou | H04N 23/51 348/78 |

OTHER PUBLICATIONS

Atchison et al., "Useful Variations of the Badal Optometer," Optom. Vis. Sci. 72, pp. 279 to 284, 1995.

Thibos et al., "Power vectors: An Application of Fourier Analysis to the Description and Statistical Analysis of Refractive Error," Optometry and Vision Science, vol. 74, No. 6, pp. 367 to 375, 1997.

Asatryan et al., "Optical lens with electrically variable focus using an optically hidden dielectric structure," Optics Express, vol. 18, No. 13, pp. 13981 to 13992, Jun. 2010.

Charman et al., "Peripheral refraction and the development of refractive error: a review," Ophthalmic Physiol. Opt., vol. 30, No. 4, pp. 321 to 338, Jul. 2010.

Vinas et al., "Longitudinal chromatic aberration of the human eye in the visible and near infrared from wavefront sensing, double-pass and psychophysics," Biomedical Optics Express, vol. 6, Issue 3, pp. 513 to 522, Feb. 2015.

Industrial Norm "Ophthalmic optics—Spectacle lenses—Vocabulary (ISO 13666:2012)," German and English version EN ISO 13666:2012, Oct. 2013.

European Search Report issued in EP 20 198 056.2 to which this application claims priority of, dated Feb. 25, 2021.

International Search Report and Written Opinion issued in PCT/EP2021/000112 to which this application claims priority, dated Apr. 14, 2022.

International Preliminary Report on Patentability issued in PCT/EP2021/000112 to which this application claims priority, dated Dec. 19, 2022.

* cited by examiner

APPARATUS AND METHOD FOR DETERMINING THE REFRACTIVE ERROR OF AN EYE

CROSS REFERENCE TO RELATED APPLICATIONS

This application is a continuation application of international patent application PCT/EP2021/000112, filed on Sep. 24, 2021 and designating the U.S., which claims priority to European patent application EP 20 198 056.2, filed on Sep. 24, 2020, both of which are hereby incorporated by reference in their entireties.

TECHNICAL FIELD

The present application relates to apparatuses and methods for determining the refractive error of an eye.

BACKGROUND

Determining the refractive error of an eye is an important part of eye examinations, the result of which is for example used to produce lenses for eyeglasses with appropriate optical properties for the respective eye or to prescribe appropriate contact lenses. In the field of ophthalmology, the refractive error of an eye is usually given in terms of sphere, also referred to as spherical power, as defined in 11.2 of DIN EN ISO 13666:2013-10, cylinder, or also referred to as cylindrical power, as defined under 12.5 of DIN EN ISO 13666:2013-10 and axis, more precisely cylinder axis, as defined under 12.6 of DIN EN ISO 13666:2013-10. These values give essentially the deviations from an emmetropic eye (zero refractive error). Values of 0 for sphere and cylinder indicate that the eye is emmetropic, while values different from 0 indicate various kinds of ametropia like hyperopia or myopia.

A determination of the refractive error may be a subjective refractive error determination or objective refractive error determination. Methods for subjective refractive error determination are based on a (subjective) feedback of an examined person regarding his or her visual perception. An example is a measurement on the basis of eye charts with small and smaller symbols, letters, numbers or the like, where the person gives feedback which numbers, letters or symbols he or she can recognize. Lenses may then be placed in front of the eye of the person, and the person may give feedback with which lenses the best visual perception is obtained. An example for apparatuses allowing subjective refractive error determinations are phoropters. Methods and apparatuses for objective refractive error determination do not need such a feedback of the examined person regarding his or her visual perception.

Examples for apparatuses for objective refractive error determination are Hartmann-Shack-based aberrometers, as for example described in G. Colicchia and H. Wiesner, Physics Education, Volume 41, No. 4. Such aberrometers are comparatively complex and therefore are costly apparatuses which require a camera and lenslet array for sensing wavefronts. The measurement range of such aberrometers is limited by the parameters of the lenslet array and is inversely proportional to the accuracy, i.e., a higher measurement range typically will result in lower accuracy. WO 2013/165689 discloses an ophthalmic wavefront sensor which requires a wavefront sensor, a camera and lenslet array having apertures with identical circular shape, thus is expected to have similar problems in terms of complexity and accuracy.

Another class of apparatuses used for objective refractive error determination referred to as autorefractors are based on principles described in Spanish patent application ES 482663 A1 and are available commercially in many forms, for example as the Zeiss Visuref 100 or 150. Such autorefractors often exhibit a comparatively low accuracy compared to aberrometers, in particular in case of a positive refractive error, i.e., hyperopic subjects. Therefore, the result of such autorefractors is often only used as a starting point to then perform a subjective refractive error determination as a more exact measurement.

Furthermore, current solutions of aberrometers and autorefractors usually do not offer the possibility to include possibilities for such subjective refractive error determination without significant changes of the optical design. Finally, conventional aberrometers and autorefractors do not provide natural viewing conditions, i.e., the person has to look into the instrument and does not naturally perceive his or her surroundings. This may lead to so-called "instrument myopia," i.e., myopia measured because of the particular measurement conditions outside natural viewing conditions, which do not correspond to actual ametropia of the eye.

U.S. Pat. No. 4,376,573 and U.S. Pat. No. 4,293,198 provide an apparatus for measuring the refractive power of the eye. Here, a light receiving mask having three slits which are formed perpendicularly to one of the radii forming 120° with each other and are spaced apart from the optic axis is disclosed.

SUMMARY

Starting from such conventional apparatuses for objective refractive error determination and corresponding methods, it is an object of the present disclosure to provide apparatuses and methods which are capable of remedying at least some of the drawbacks above, in particular which may be designed for a large measurement range, may be easily designed to allow natural viewing conditions or allow integration of a subjective refractive error determination. The present disclosure provides more room for diversified measurements of light intensities for calculating the refractive power and may also increase accuracy of the measurements.

An apparatus for determining the refractive error of an eye containing at least three different apertures that are provided in at least three different locations and a method for determining the refractive error of an eye based on the intensities for each of the at least three different apertures are provided. Exemplary embodiments as well as a method for manufacturing lenses for spectacles are discussed below.

According to a first aspect of the disclosure, an apparatus for determining a refractive error of an eye is provided, comprising:
 an illumination device,
 an aperture device, and
 a detector device configured to measure an intensity of light coming from the eye through the aperture device.

The apparatus is characterized in that the aperture device is configured to provide at least two or at least three different apertures, the detector device is configured to measure the intensities of light for each of the different apertures of the aperture device. Furthermore, the apparatus is further characterized by further comprising a computing device configured to determine the refractive error based on the intensities for each of the different apertures.

An aperture is an optical element which is an opening where light may pass through. An aperture device as used herein is configured to provide the same or different apertures. The aperture device can comprise at least two or at least three different apertures. The aperture device is designed to block light in the parts other than opening(s) of the apertures. The aperture device as used herein is not configured to receive light directly coming from the illumination device. The aperture device is configured to receive light coming from the eye. Only the light passes through the apertures of the aperture device enters the detector device, which will be further explained below. The term "aperture device" does not imply that the device or apertures have to be in one piece or in one location. For example, the at least two or at least three different apertures may be provided in two or three different locations simultaneously.

Apertures are the same as or different from each other in terms of shape, arranged orientation or both. It should be noted that the different apertures, as will be explained later, need not be physically separate apertures, but may also be a single physical aperture which can be arranged in various orientations.

Likewise, a detector device refers to any device which is capable of measuring at least light intensity. The detector device is configured to measure an intensity of the light coming from the eye and through the apertures of the aperture device. It may be capable of measuring further properties of light, like a beam shape or shape of a focal spot of light falling on the detector device. For example, for measuring only the light intensity, a photodiode may be used. For measuring further properties, an image sensor as used in digital cameras or a camera itself may be used. As for the aperture device, the detector device needs not be provided in one piece, but may include separate detectors for each aperture.

"Intensity" refers to the power or energy of the light beam. It may be measured as an integrated intensity over a detector area.

The refractive error may be indicated as sphere, cylinder, and axis as mentioned above.

A computing device refers to any device capable of determining the refractive error based on calculations and, where necessary, of controlling the apparatus. Such a computing device may be implemented as a conventional computer program accordingly, with interfaces for example to the detector device, or other components described below, a microcontroller, application-specific integrated circuits (ASICs) or combinations of such components.

With such an apparatus, the refractive error may be determined precisely with a compact device.

Generally speaking, the detector device may be used to measure the intensity of a respective point spread function (PSF) or its approximation, specific for the respective aperture over the area of detector, and based on the intensities of the point spread function over the area of the detector, the refractive error may be determined. As will be explained below, in exemplary embodiments the area of the detector is selected to cover a limited area only, such that a comparatively small area of the point spread function is measured. The point spread function generally describes the response of an imaging system, which in this case includes the at least two apertures, to a point source. If a light source other than a point source is present, what is measured is an approximation of the point spread function.

In some exemplary embodiments, the different apertures may include at least three different apertures. With three different apertures, the refractive error in terms of sphere, cylinder, and axis may be determined without further information or measurement.

Alternatively, the cylinder axis value, i.e., the axis as defined under 12.6 of DIN EN ISO 13666:2013-10, may be determined in advance by conventional measurements, for example by using an eye chart with rays depicted under different angles and determining, by subjective feedback from the person, in which direction the rays appear sharpest. In this case, as the axis is given, two different apertures are sufficient to determine the remaining two values of sphere and cylinder. In other cases, for example a value of the sphere may be known from other measurements. Also in this case, measurement with two apertures are sufficient to determine the remaining values, namely cylinder and axis.

It should be noted that the measurement may be repeated for more than three (in case of at least three different apertures) or more than two different apertures (in the case where e.g. axis or sphere is known in advance and only at least two different apertures are required), respectively. As is generally the case for measurements, making more measurements than required may help to reduce a measurement error.

Typically, the apparatus further comprises an optical power changing device which changes the optical power of the light path from the eye to the detector device. The optical power of the light path determines the size and focus how the light from the eye is imaged to the detector. In some exemplary embodiments, the optical power changing device may include a variable focus optic. A variable focus optic generally is an optical device the focal length of which may varied. Such a variable focus optic may for example comprise one or more lenses, a focal length of which may be varied. Such lenses may for example include a lens with electrically variable focus as discussed in K. Asatryan et al., Optics Express, Volume 18, No. 13, liquid lenses, or an optic with two or more lenses, some of which are movable with respect to other lenses. Other examples include lens- or mirror-based Badal systems (D. A. Atchison, A. Bradley, L. N. Thibos, and G. Smith, "Useful Variations of the Badal Optometer," Optom. Vis. Sci. 72, 279-284 (1995)), deformable mirrors, spatial light modulators (SLMs) or a set of polarization-dependent lenses.

The variable focus optic may be placed at different locations in the light path, for example between the eye and the aperture device, or also between the aperture device and the detector device, or also inside the aperture device. When the two or more apertures are provided separately with separate detectors of the detector device, the variable focus optic may include separate components for each aperture/detector combination.

Another example for an optical power changing device causes axial movement of fixed focal length lenses within the system, or of the detector device. A range through which the optical power of the optical power changing device can be varied corresponds to a measurement range of the apparatus. By providing on optical power changing device with a wide range of optical power settings, a correspondingly large measurement range may be easily obtained.

For determining the refractive error of an eye, the computing device may control the optical power changing device to vary the optical power, while the intensities are measured for each of the different apertures. Maximum values of the intensity may then be identified by the computing device, and the calculation may be based on optical power settings of the optical power changing device at the respective maximum intensity for each of the different apertures. A similar approach may be taken of the change of optical power is provided computationally. Also here, optical powers for each aperture where a maximum intensity is present in a detection area may be determined.

In this case, simple integrated intensity measurements may be used. This enables the use of simple detectors in the detector device, for example one or more photodiodes.

The at least two apertures may include at least two slit-shaped opening. A slit-shaped opening refers to a shape similar to or a slit which has a significantly longer length than width, for example a length at least three times, at least four times or at least five times the width. A length of the slit may be similar to the physiological diameter of human's pupil, of the order of 2 to 8 mm, and a width may be less than 1 mm, typically less than 0.4 mm, more typically less than 0.2 mm. Smaller widths generally increase measurement accuracy, but on the other hand such a slit-shaped opening provides a wide diffraction limited point spread function in the width direction of the slit, and an aberration limited point spread function in the length direction of the slit. As a detector, typically a circular shaped photodiode with a diameter similar to a diameter of point spread function produced by an aberration-free human eye (for physiological pupil sizes) may be used, such that essentially the intensity determined by the aberration limited point spread function is measured. In exemplary embodiments, the diameter of the photodiode, or more generally a diameter of a detector device used is much smaller than the diffraction limited point spread function or more generally openings of the apertures of the aperture device, for example at least 2 times smaller, at least 3 time smaller, or at least 5 times smaller. The detector device with smaller diameter enables to provide the apparatus for determining a refractive error of an eye having smaller size, less complex structure, and portability.

"Diffraction limited" in this case means that the point spread function resulted is limited by diffraction phenomena at the aperture of the apparatus, or the eye. In contrast, "aberration limited" means that the point spread function is determined by aberrations/optical properties of the eye.

In case at least three different apertures are used as mentioned above, two slit-shaped openings which are arranged in different directions or orientations may be used, or, in other words, the slit-shaped openings lie in different orientations or directions may be used. With slit-shaped openings, in particular axis and/or cylinder may be measured.

In addition, one of the at least three apertures may have a circular opening. The circular opening has a diameter similar to typical physiological eye pupil sizes, i.e., in the range of 2 to 8 mm. Based on such a circular shape, the sphere of the refractive error may be determined.

In a particularly typical exemplary embodiment, three apertures are used, a first aperture with a slit-shaped opening orientated in a horizontal direction (left/right direction of the head), a second aperture also with a slit-shaped opening wherein a length direction of the opening is arranged at an angle of 45° thereto, and a third aperture with the above-mentioned circular opening. With the two slit-shaped openings, the optical power of the optical power changing device (or for computationally varied optical power) at the maximum essentially corresponds to the Jackson Cross cylinder components, with added spherical equivalent (L. N. Thibos, W. Wheeler, and D. Homer, "Power vectors: an application of Fourier analysis to the description and statistical analysis of refractive error," Optom. Vis. Sci. 75,367-375 (1997)). With $P_0$, $P_{45}$, and M being the respective optical power settings in Dioptres (D) of the optical power provided by the optical power changing device or computationally varied optical power in the pupil plane of the eye in terms of a deviation from a 0 setting for the first second and third apertures, respectively, power vectors $J_0$, $J_{45}$ can be calculated according to $$J_0 = P_0 - M$$

$$J_{45} = P_{45} - M$$

From that, the cylinder J may be calculated according to $$J = \sqrt{J_0^2 + J_{45}^2},$$

and the axis $\alpha$ may be calculated according to $$\alpha = \frac{1}{2}\tan^{-1}(J_{45}/J_0).$$

When only two apertures are present, M corresponds to the sphere. In case where there are at least three apertures, M is the optical power setting at maximum intensity for the third aperture.

In an alternative exemplary embodiment, instead of the third aperture with a circular opening, a third aperture with a slit-shaped opening at an angle of 90° with respect to the slit-shaped opening of the first aperture may be used. In that case, the first and second apertures are used as above to measure values $P_0$, $P_{45}$, and with the third aperture a value $P_{90}$ is measured corresponding to an optical power at maximum intensity for the third aperture. For the calculations above, then for M an average value of $P_0$ and $P_{90}$ is taken ($M=(P_0+P_{90})/2$). Other apertures, for example with slit-shaped openings arranged at the angles other than 0°, 45°, or 90°, may also be used. This may lead to more complex calculations or to reduced accuracy.

The apparatus may further include an illumination device for creating a focal spot on the subject's retina through the measurement, which, when back-propagated, produces aperture-modified point spread functions (of the point corresponding to the focal spot) on the detector device. In case a non-point light source like a light emitting diode, LED, is used, the detector device measures essentially a superposition of all point spread functions of points of the light on the eye. This, as mentioned above, may be seen as an approximation of the point spread function and may also be used for measurements as described herein. Therefore, a point light source like a focused laser is not required. Typically, the illumination device uses infrared light, in particular an infrared laser. In this way, the person examined does not notice the light used for the measurement. Such an illumination device may be placed at various parts of the apparatus, and light may be guided to the eye using elements like mirrors, including for example a semitransparent mirror, and/or lenses.

However, due to chromatic aberration of the eye, the values of sphere, cylinder, and axis thus calculated using infrared light differ from the values for visible light, for which lenses ultimately have to be designed. Therefore, a correction of this deviation due to chromatic aberration of the optical power of the eye as a function of wavelength may be performed in some exemplary embodiments, for which previously reported values of longitudinal chromatic aberrations may be used, such as in M. Vinas, C. Dorronsoro, D. Cortes, D. Pascual, and S. Marcos, "Longitudinal chromatic aberration of the human eye in the visible and near infrared from wavefront sensing, double-pass and psychophysics,"

Biomed. Opt. Express 23, 513-522 (2015). For instance, chromatic shift from 555 nm to 780 nm would be around 0.8 D. Then, for calculating the refraction values, 0.8 D should be subtracted from M, $P_0$, and $P_{45}$ as used in the equations above.

The different apertures may be provided in different manners. In some exemplary embodiments, at least partially separate light paths from the eye may be provided for each of the apertures, and each light path may include a detector of the detector device. "Partially separate" indicates that the light paths may have a common part, which then splits up for the separate light paths. In this case, the intensity measurement for the different apertures may be performed simultaneously, thus reducing the measurement duration. In other exemplary embodiments, the aperture device may be configured to accommodate exchangeable apertures, such that the different apertures may be provided temporarily one after the other. This may allow for a more compact design of the apparatus, as only a single light path with corresponding detector is needed, but this may also extend measurement time. In yet other exemplary embodiments, for example a rotatable aperture with a slit-shaped opening may be provided, and the different apertures correspond to the slit-shaped opening in different rotation positions.

The apparatus may further include a visible light path which may allow the eye to view surroundings of the person examined. Such a viewing path may be separated from the aperture device and detector device by a short pass mirror which allows only light used for measurement, for example infrared light, to be reflected, while visible light coming from the aperture device or the detector device is blocked, such that the person cannot see the aperture device and detector device. In some exemplary embodiments, a stimulus may be provided in the visible eye path to be viewed by the eye. This may determine an accommodation state of the eye for the measurement, i.e., a distance to which the eye is focused. In some exemplary embodiments, the stimulus may include an eye chart. This enables the apparatus additionally to be used as a phoropter, i.e., for subjective refractive error determination, for example by varying the focus, cylinder, or axis of the optical power changing device mentioned above and receiving feedback from the person at which focus setting he or she views the eye chart best.

The detector device may include single photodiodes, for example one photodiode for measuring the intensity for each of the different apertures in case of different light paths, or a single photodiode in case of exchangeable apertures or a rotating aperture. In this way, an inexpensive implementation of the detector device is possible. However, other kinds of detectors like cameras may also be used.

In some exemplary embodiments, the apparatus may include a scanner module provided in a conjugate pupil plane of the eye. With such a scanner module, the retina of the eye may be scanned, i.e., the refractive error determination may be performed for different points of the retina. In this way, peripheral refractive error of the eye may be measured.

According to another aspect, a corresponding method for determining a refractive error of an eye is provided, comprising measuring an intensity of light coming from the eye through an aperture device. The method is characterized in that the intensity of light is measured for at least two or at least three different apertures through which light is coming from the eye, and in that the method further comprises determining the refractive error based on the intensities for each of the different apertures.

The various variations, modifications and additions described for the apparatus may be applied to the method in a corresponding manner. For example, the method may include varying an optical power setting of an optical power changing device and then, determining, for each of the different apertures, a focus setting which the intensity is at a maximum, and determining the refractive error based on the focus settings.

The thus determined refractive error may then be used for producing lenses using the refractive error, i.e., lenses to correct the refractive error of the eye.

A computer program may also be provided which, when executed on a computing device, causes the computing device to control an apparatus as explained above to perform the method as explained above.

BRIEF DESCRIPTION OF THE DRAWINGS

Various exemplary embodiments will now be described referring to the attached drawings, wherein.

DESCRIPTION OF EXEMPLARY EMBODIMENTS

Figure 1:
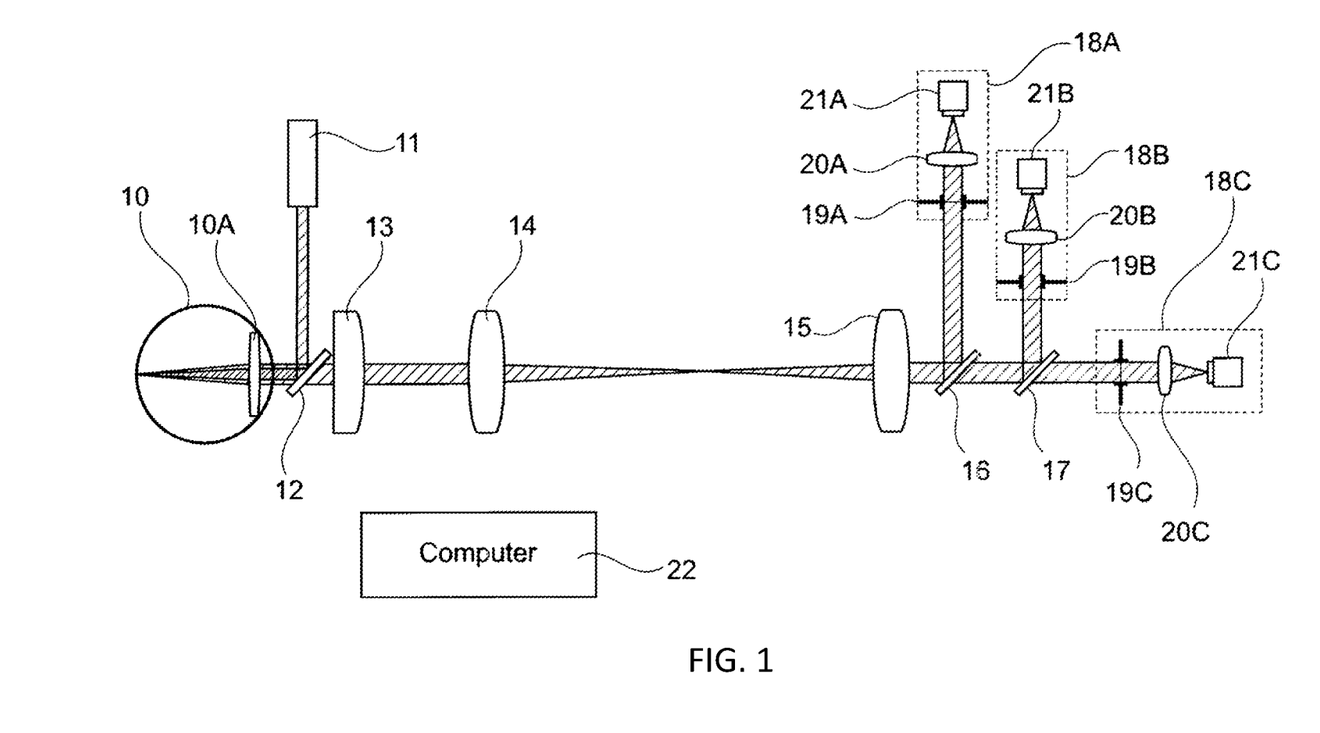
FIG. 1 is an apparatus for determining the refractive error of an eye according to an exemplary embodiment.

FIG. 1 is a diagram illustrating an apparatus for determining refractive error of an eye 10 having optical properties represented by a lens 10A according to an exemplary embodiment.

It should be noted that while single lenses are depicted in several instances in the following exemplary embodiments, these may be replaced by combinations of two or more lenses, or by other optical elements like diffractive elements having the same or similar optical function.

The apparatus of FIG. 1 includes an infrared laser 11 as an illumination device. Light from infrared laser 11 is reflected by a semitransparent mirror 12 through lens 10A into eye 10.

By using an infrared laser, or infrared light in general, the person examined (i.e., the person to whom eye 10 belongs) does not notice the examination.

Light reflected from the retina of eye 10 through lens 10A passes through semitransparent mirror 12, a focus adjustable lens 13 and an optics arrangement including lenses 14 and 15. Focus adjustable lens 13 is a simple example for an optical power changing device and may be implemented as explained above, for example using an adjustable liquid lens, or any of the other possibilities mentioned above, including an arrangement of several lenses or other optical elements as well as moving lenses or detectors. The placement of focus adjustable lens 13 is also only an example, and as explained above other placements may be used.

Lenses 14, 15 form a telescope arrangement guiding the light to a first semitransparent mirror 16 followed by a second semitransparent mirror 17.

First semitransparent mirror 16 passes a part of the light to a first module 18A and passes another part of the light on to semitransparent mirror 17. Semitransparent mirror 17 reflects part of the light to a second module 18B and passes another part of the light on to a third module 18C. The amount of light provided to each of modules 18A to 18C may be approximately the same, but also may be different from each other.

Each of first to third modules 18A to 18C comprises a respective aperture 19A, 19B, 19C, respectively, and a respective lens 20A, 20B, 20C, respectively, for passing light to a respective detector 21A, 21B, 21C, respectively. Apertures 19A, 19B, and 19C are different from each other. Detectors 21A, 21B, and 21C in the exemplary embodiment of FIG. 1 are photodiodes. Apertures 19A, 19B, and 19C are examples for an aperture device and detectors 21A, 21B, and 21C are examples for a detector device.

As explained above, instead of three modules 18A, 18B, and 18C, also a single module (for example module 18C, with semitransparent mirrors 16, 17 being omitted) may be provided. In this case, module 18C may have an exchangeable aperture, such that three different apertures may be inserted consecutively. In other exemplary embodiments, in this case aperture 19C may be a rotatable aperture with a slit-shaped opening, as explained above.

Furthermore, in cases where the cylinder axis or the sphere of the refractive error are already known, as explained above, only two different apertures may be needed. In such exemplary embodiments, one of the modules 18A, 18B, or 18C may be omitted.

The apparatus of FIG. 1 additionally includes a computer 22. Computer 22 controls a focal setting of focus adjustable lens 13, receives detected intensities from detectors 21A, 21B, and 21C, and calculates the refractive error of eye 10, more particularly of lens 10A thereof, in terms of sphere, cylinder, and axis.

Figure 2:
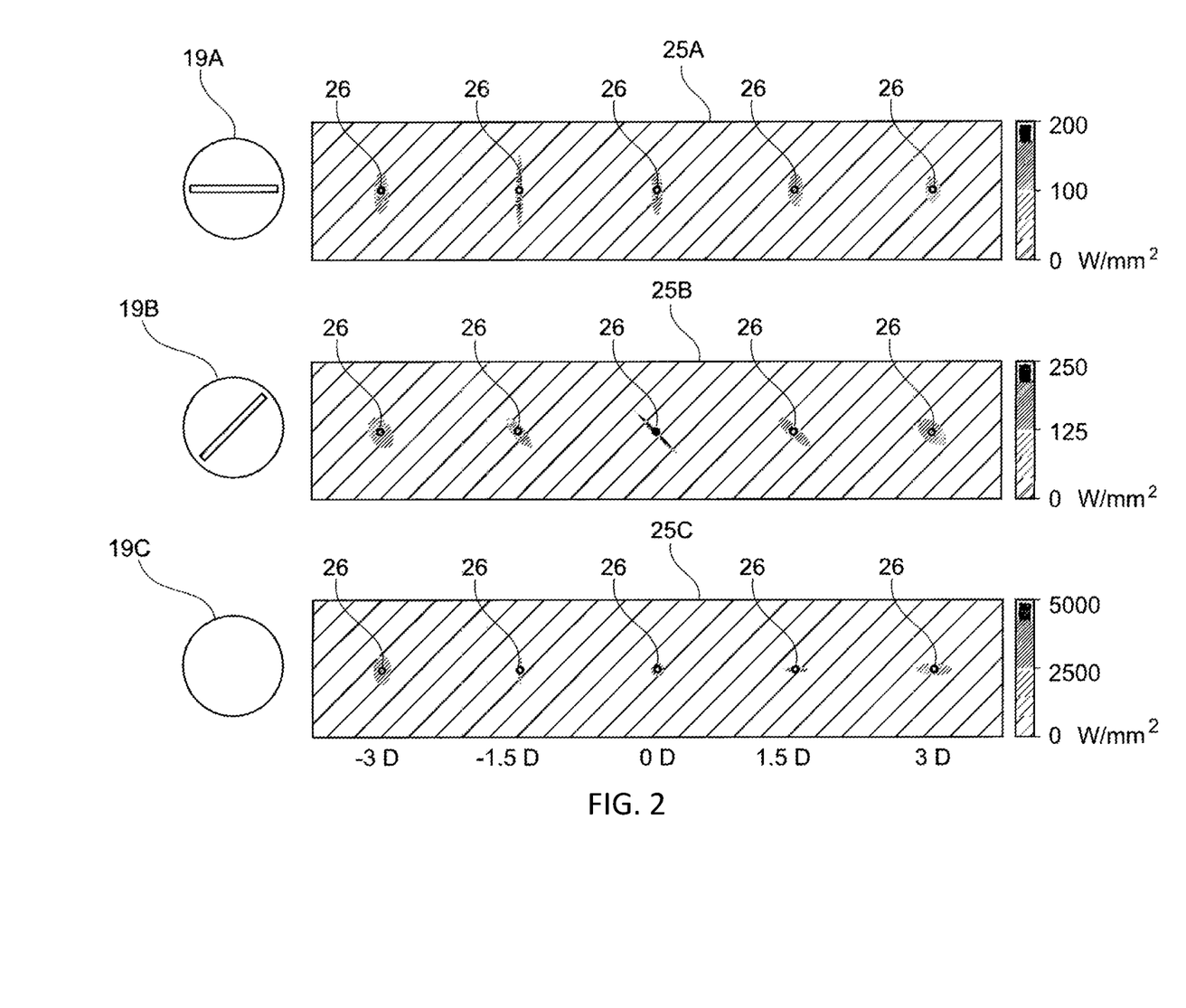
FIG. 2 is a diagram showing apertures and measurement results to illustrate exemplary embodiments.

To further illustrate such a measurement, FIG. 2 shows examples for apertures 19A, 19B, and 19C and associated measurements.

Aperture 19A has a slit running in a horizontal direction. This slit-shaped opening leads to a wide diffraction limited point spread function in one meridian of the eye (in this case perpendicular to the slit), and an aberration limited point spread function in the medium perpendicular thereto. A graph 25A shows resulting intensity distributions after the aperture for different optical power settings of focus adjustable lens 13 of −3 D, −1.5 D, 0 D, 1.5 D and 3 D. An optical power setting of 0 D corresponds to the case where the point spread function an emmetropic (aberration-free) eye is in focus on detectors 21A-21C. For measurement, variable focus lens 13 is scanned through a range of optical power settings. Corresponding intensities are measured with photodiode 21A. The diameter of the photodiode is much smaller than the diffraction limited point spread function, for example at least 2 times smaller, at least 3 time smaller, or at least 5 times smaller. To illustrate an example, the detection area of the detectors 21A, 21B, 21C, respectively, is marked with reference numeral 26 throughout FIG. 2.

In this example, the maximum intensity is detected by photodiode 21A at the optical power setting of −1.5 D, which may be seen as a focal shift or defocus change in this case. The value for which this maximum is detected depends on the refractive error of the eye, in lens 10A and length, and therefore the maximum at −1.5 D is merely a specific example.

Aperture 19B is also slit-shaped and the opening is tilted in an angle of 45° compared to the opening of the slit-shaped aperture 19A. Here, intensities are measured by photodiode 21B, with the maximum intensity in this case being measured at 0 D.

Third aperture 19C has a circular opening of a diameter similar to typical physiological eye pupil sizes. The intensity is detected by photodiode 21C. Photodiode 21C in this case has a diameter similar to the airy disc produced by the aperture 19C, the airy disc corresponding to a best focus spot of light that a perfect lens with the circular aperture 19C can make, limited by the diffraction of light. In particular, the photodiode size may be half the diameter of the airy disc ±50%, typically ±20%. In this example, the maximum intensity is then detected at 0 D.

As mentioned, for measurement computer 22 controls variable focus lens 13 to scan through a range of focus settings (in the example of FIG. 2, from −3 D to 3 D in steps of 1.5 D), and computer 22 receives the intensities measured by detectors 21A, 21B, and 21C and determines the focus setting where the intensity is at a maximum. In the example of FIG. 2, as mentioned this would be at −1.5 D for aperture 19A, at 0 D for aperture 19B and at 0 D for aperture 19C. With Po being the optical power setting at the maximum intensity for aperture 19A, and $P_{45}$ the optical power setting at the maximum intensity for aperture 19B, and M the optical power setting at the maximum intensity for aperture 19C as mentioned cylinder J and axis a may be calculated according to:

$$J_0 = P_0 - M,$$

$$J_{45} = P_{45} - M,$$

$$J = \sqrt{J_0^2 + J_{45}^2}, \text{ and}$$

$$\alpha = \frac{1}{2}\tan^{-1}(J_{45}/J_0).$$

The sphere directly follows from the maximum intensity for aperture 19C, i.e., is equal to M. In the example of FIG. 2, 0 D may indicate that there is no spherical aberration, i.e., equivalent sphere=0 D.

Next, additions to the exemplary embodiment of FIG. 1 will be described referring to FIGS. 3 and 4. Components already discussed with reference to FIGS. 1 and 2 bear the same reference numerals and thus will not be described again. In particular, apart from differences pointed out below, operation of the exemplary embodiments of FIGS. 3 and 4 is the same as for the exemplary embodiments of FIG. 1.

Figure 3:
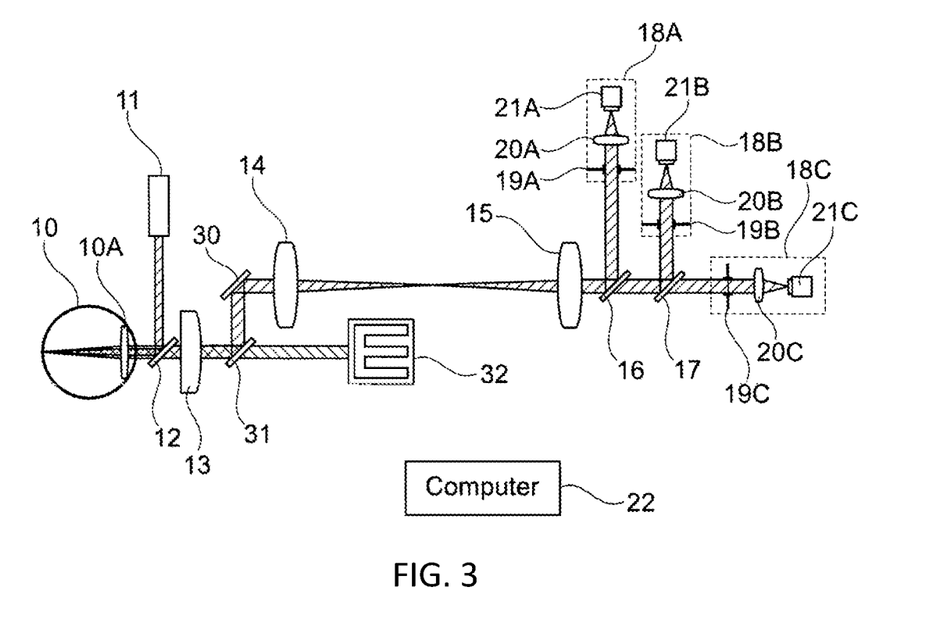
FIG. 3 shows an apparatus for determining the refractive error of an eye according to a further exemplary embodiment.
Figure 4:
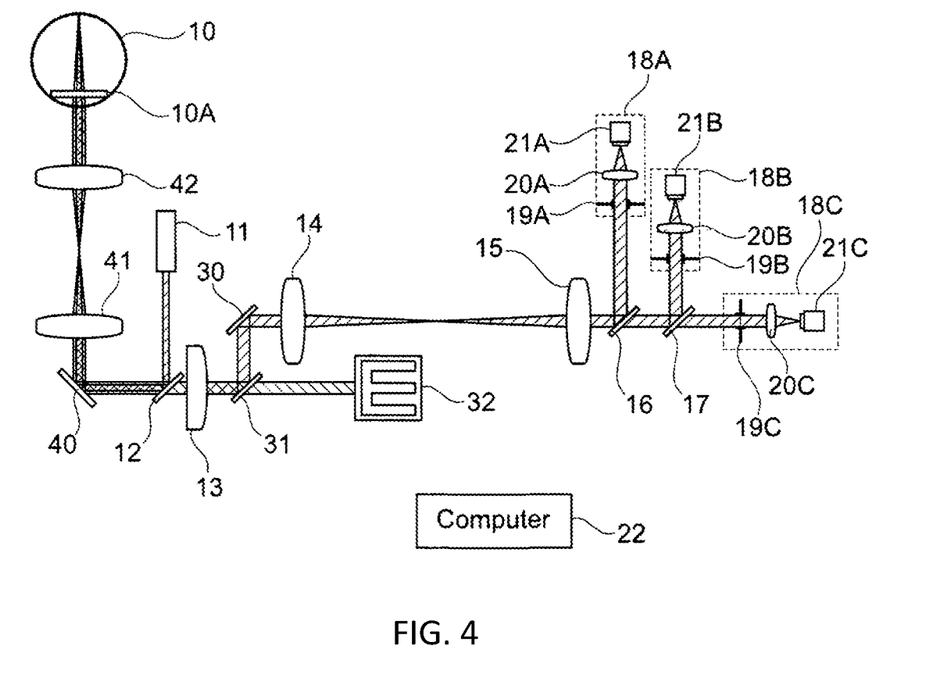
FIG. 4 shows an apparatus for determining the refractive error of an eye according to a further exemplary embodiment.

In the exemplary embodiment of FIG. 3, a light path for visible light is added. To this end, a short pass mirror 31 is provided. Mirror 31 reflects only light in the infrared range and lets light in the visible range pass through. Such mirrors may for example be implemented by using respective coating layers. In this way, the light from infrared laser 11 as reflected by the retina of light 10 goes through to a mirror 30 and then to lenses 14, 15 already described. Further, visible light from lenses 14, 15 and modules 18a to 18c does not come to eye 10, as it is not reflected by short stop mirror 31, and therefore these measurement components are not seen by the person examined. Furthermore, as short pass mirror 31 is transparent to visible light, eye 10 may view the surroundings or other elements through short pass mirror 31. This may also be referred to as providing a visible channel or visible light path. This enables the refractive error measurement described above to be performed under natural viewing conditions for eye 10.

In the exemplary embodiment of FIG. 3, a stimulus 32 is provided in this visible path to be viewed by the person during the measurement, to bring eye 10 to a certain accommodated state (for example focused on a nearby object if stimulus 32 is provided near eye 10, focus on a far object if stimulus 32 is provided farther away) or while varying the accommodation, by effectively moving stimulus 32. Effectively moving may include moving stimulus 32 itself or providing a variable optic in front of stimulus 32. This additionally may help to reduce instrument myopia, thus leading to a higher accuracy of the measurement. For changing the perceived distance of stimulus 32, a further focus adjustable lens may be provided in front of element 32.

In this way, the refractive error during accommodation to a new distance may be measured.

In some exemplary embodiments, stimulus 32 may be an eye chart. This eye chart may be any conventional eye chart, for example Snellen chart, and may be displayed on a computer screen or provided on a wall to be viewed through short pass mirror 31. Using this eye chart, the apparatus of FIG. 3 may additionally be used as a phoropter, i.e., for subjective refractive error determination. As can be seen, no significant modifications to the apparatus are necessary for this, but compared to FIG. 1, only short pass mirror 31, mirror 30 and eye chart as stimulus 32 are additionally provided. For subjective refractive error measurement, the focal setting of variable focus lens 13 may be varied, and the person examined may indicated at which focal setting he/she can best see letters, numbers, symbols, etc. displayed on the eye chart.

FIG. 4 illustrates a further exemplary embodiment. In addition to the exemplary embodiment of FIG. 4, a scanning module 40 is provided in a conjugated plane to the pupil of eye 10, with respect to a telescope optic formed by lenses 41, 42.

In FIG. 4, the scanning module is represented by a rotational mirror. Combinations of several mirrors or other optical elements may also be used.

Via scanning module 40, the focus spot light beam from infrared laser 11 may essentially be scanned over the retina of eye 10. In this way, the refractive error of the eye may be determined for a visual field of eye 10. In particular, also a so-called peripheral refractive error for a periphery of the retina may be measured. This may for example be used for evaluating myopia development, see W. Neil Charman and H. Radhakrishnan, "Peripheral refraction and the development of refractive error: A review," Ophthalmic Physiol. Opt. 30, 321-338 (2010).

Figure 5:
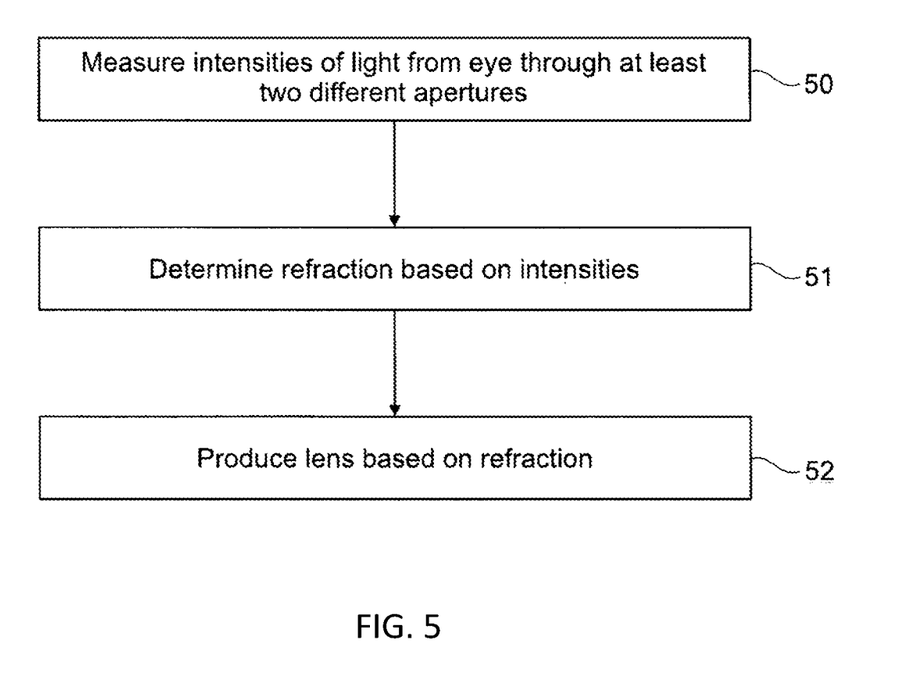
FIG. 5 is a flowchart illustrating a method according to exemplary embodiment.

FIG. 5 is a flowchart illustrating a method according to an exemplary embodiment. The method of FIG. 5 may be implemented using the apparatuses discussed with reference to FIGS. 1, 3 and 4 and in order to avoid repetitions, the method of FIG. 5 will be explained referring to the previous explanations.

At step 50 in FIG. 5, intensities of light from the eye are measured through at least two different apertures, for example through the three apertures 19A, 19B, and 19C discussed previously. Without any additional information, at least three different apertures are used. In implementations where, as mentioned above, the axis (angle a in the formula above), or sphere (value M in the formula above) is known from other measurements, two apertures are sufficient. For example, the intensities may be measured in step 50 depending on a focal setting of a focus adjustable lens like focus adjustable lens 13.

In step 51, the reflection of the eye is determined based on the intensities, for example by identifying at which focus setting the intensities are at their maximum for the respective aperture and then determining the refractive error based on these focus settings, as explained above referring to FIG. 2.

The determined refractive error may then be used for producing a lens for spectacle glasses based on the refractive error to correct the refractive error. To this end, the determined refractive error is transmitted to a lens manufacturer.

Some exemplary embodiments are defined by the following clauses:

Clause 1. An apparatus for determining a refractive error of an eye (10), comprising: an illumination device (11), an aperture device (19A, 19B, 19C) configured to provide at least three different apertures and configured to receive light coming from the eye (10) through the different apertures of the aperture device (19A, 19B, 19C), and a detector device (21A, 21B, 21C) configured to measure an intensity of the light coming from the eye (10) through each of the different apertures of the aperture device (19A, 19B, 19C), characterized in that the different apertures comprise a first aperture with a first slit-shaped opening, a second aperture with a second slit-shaped opening and a third aperture with a circular opening.

Clause 2. The apparatus of clause 1, characterized by further comprising at least one of:

an optical power changing device (13), wherein the computing device (22) is configured to control the optical power changing device (13) to vary an optical power of a light path from the eye (10) to the detector device (21A, 21B, 21C) through a measurement range, or the computing device (22) being configured to computationally vary an optical power of a light path from the eye (10) to the detector device (21A, 21B, 21C) through a measurement range, and characterized in that the computing device (22) is further configured to determine optical power settings at a maximum intensity for each of the at least three apertures, and to determine the refractive error based on the optical power settings at maximum intensity.

Clause 3. The apparatus of clause 1 or 2, characterized in that the two slit-shaped openings are arranged in different directions.

Clause 4. The apparatus of any one of clauses 1 to 3, characterized in that the computing device (22) is configured to determine a sphere of the refractive error based on the optical power setting at maximum intensity for the third aperture.

Clause 5. The apparatus of any one of clauses 2 to 4 characterized in that a first slit-shaped opening of the two slit-shaped openings has a longitudinal direction of the slit in a horizontal direction with respect to the eye (10), a second slit-shaped opening of the two slit-shaped openings is arranged at an angle of 45° with respect to the longitudinal direction of the first slit-shaped opening, Clause 6. The apparatus of clause 5,
characterized in that
a cylinder J and an axis a are calculated according to:

$$J_0 = P_0 - M$$
$$J_{45} = P_{45} - M$$
$$J = \sqrt{J_0^2 + J_{45}^2}, \text{ and}$$
$$\alpha = \frac{1}{2}\tan^{-1}(J_{45}/J_0)$$

wherein $P_0$ is the optical power setting in Dioptres at maximum intensity for the first slit-shaped opening, $P_{45}$ is the optical power setting at maximum intensity for the second slit-shaped opening, and M is the optical power setting at maximum intensity for the third aperture.

Clause 7. The apparatus of any one of clauses 1 to 6, characterized in that
the apparatus comprises separate light paths for each of the different apertures, and wherein the detector device (21A, 21B, 21C) comprises separate detectors for each of the different apertures.

Clause 8. The apparatus of any one of clauses 1 to 7, characterized in that
the aperture device (19A, 19B, 19C) is configured to provide the different apertures as exchangeable apertures.

Clause 9. The apparatus of any one of clauses 1 to 8, characterized in that
the aperture device (19A, 19B, 19C) is configured to provide the different apertures by rotating a slit-shaped opening.

Clause 10. The apparatus of any one of clauses 1 to 9, characterized in that
the apparatus further comprises a visible light path separate from the aperture device (19A, 19B, 19C) and the detector device (21A, 21B, 21C).

Clause 11. The apparatus of clause 10, characterized by further comprising a stimulus (32) in the visible light path to be viewed by the eye (10).

Clause 12. The apparatus of clause 11, characterized in that
the stimulus (32) comprises an eye chart.

Clause 13. The apparatus of any one of clauses 1 to 12, characterized by further comprising a scanning module (40) arranged at a conjugate pupil plane to a pupil of the eye (10) and configured to scan a visual field of the eye (10).

Clause 14. A method for determining a refractive error of an eye (10), comprising:
measuring an intensity of light coming from the eye (10) through each of at least three different apertures of an aperture device (19A, 19B, 19C),
characterized in that
the method further comprises determining the refractive error based on the intensities for each of the at least three different apertures, wherein the different apertures comprise a first aperture with a first slit-shaped opening, a second aperture with a second slit-shaped opening and a third aperture with a circular opening.

Clause 15. The method of clause 14, characterized by further comprising at least one of:
varying an optical power of a light path from the eye (10) to a detector device (21A, 21B, 21C) for the detecting through a measurement range, or
computationally varying an optical power of a light path from the eye (10) to the detector device (21A, 21B, 21C) through a measurement range, and by determining optical power settings at a maximum intensity for each of the at least three apertures, and determining the refractive error based on the optical power settings at maximum intensity.

Clause 16. The method of clauses 14 or 15, characterized in that the two slit-shaped openings are arranged in different directions.

Clause 17. The method of any one of clauses 14 to 16, characterized by further comprising determining a sphere of the refractive error based on the optical power setting at maximum intensity for the third aperture.

Clause 18. The method of any one of clauses 14 to 17 characterized in that a first slit-shaped opening of the two slit-shaped openings has a longitudinal direction of the slit in a horizontal direction with respect to the eye (10) and a second slit-shaped opening of the two slit-shaped openings is arranged at an angle of 45° with respect to the longitudinal direction of the slit-shaped opening of the first slit-shaped opening.

Clause 19. The method of clause 18, characterized in that a cylinder J and an axis a are calculated according to:

$$J_0 = P_0 - M$$
$$J_{45} = P_{45} - M$$
$$J = \sqrt{J_0^2 + J_{45}^2}, \text{ and}$$
$$\alpha = \frac{1}{2}\tan^{-1}(J_{45}/J_0),$$

wherein $P_0$ is the optical power setting in Dioptres at maximum intensity for the first slit-shaped opening, $P_{45}$ is the optical power setting at maximum intensity for the second slit-shaped opening, and M is the optical power setting at maximum intensity for the third aperture.

Clause 20. The method of any one of clauses 14 to 19, characterized by further comprising providing a stimulus (32) in a visible light path to be viewed by the eye (10).

Clause 21. The method of any one of clauses 14 to 20, characterized by further comprising scanning a visual field of the eye (10).

Clause 22. A method for producing a lens for spectacle glasses, characterized by comprising:
determining the refractive error of an eye (10) according to the method of any one of clauses 14 to 21, and
producing the lens based on the determined refractive error.

Clause 23. An apparatus for determining a refractive error of an eye (10), comprising: an illumination device (11),
an aperture device (19A, 19B, 19C) configured to provide at least three different apertures and configured to receive light coming from the eye (10) through the different apertures of the aperture device (19A, 19B, 19C), and
a detector device (21A, 21B, 21C) configured to measure an intensity of the light coming from the eye (10) through each of the different apertures of the aperture device (19A, 19B, 19C),
characterized in that the different apertures comprise a first aperture with a first slit-shaped opening having a longitudinal direction of the slit in a horizontal direction with respect to the eye (10) and a second aperture with a second slit-shaped opening which is arranged at an angle of 45° with respect to the longitudinal direction of the first slit-shaped opening.

Clause 24. An apparatus for determining a refractive error of an eye (10), comprising: an illumination device (11),
an aperture device (19A, 19B, 19C) configured to provide at least three different apertures and configured to receive light coming from the eye (10) through the different apertures of the aperture device (19A, 19B, 19C), and
a detector device (21A, 21B, 21C) configured to measure an intensity of the light coming from the eye (10) through each of the different apertures of the aperture device (19A, 19B, 19C),
characterized in that
wherein the different apertures comprise a first aperture with a first slit-shaped opening and a second aperture with a second slit-shaped opening, and
wherein the detector device (21A, 21B, 21C) is circular shaped with a diameter smaller than the different apertures.

Clause 25. The apparatus of clause 23 or 24, characterized in that the computing device (22) is configured to determine the refractive error based on intensity of light for two different apertures and a cylinder axis provided to the computing device (22).

Clause 26. The apparatus of clause 23 or 24, characterized in that the computing device (22) is configured to determine the refractive error based on intensity of light for each of at least three different apertures.

Clause 27. The apparatus of any one of clauses 23 to 26, characterized by further comprising at least one of:
an optical power changing device (13), wherein the computing device (22) is configured to control the optical power changing device (13) to vary an optical power of a light path from the eye (10) to the detector device (21A, 21B, 21C) through a measurement range, or
the computing device (22) being configured to computationally vary an optical power of a light path from the eye (10) to the detector device (21A, 21B, 21C) through a measurement range,
and characterized in that the computing device (22) is further configured to determine optical power settings at a maximum intensity for each of the at least two apertures, and to determine the refractive error based on the optical power settings at maximum intensity.

Clause 28. The apparatus of any one of clauses 23 to 27, characterized in that the at least two apertures comprise/are two slit-shaped openings arranged in different directions.

Clause 29. The apparatus of any one of clauses 23 to 28, characterized in that one of the at least two apertures comprise a third aperture with a circular opening, wherein the computing device (22) is configured to determine a sphere of the refractive error based on the optical power setting at maximum intensity for the third aperture.

Clause 30. The apparatus of clause 29, characterized in that a first slit-shaped opening of the two slit-shaped openings has a longitudinal direction of the slit in a horizontal direction with respect to the eye (10), a second slit-shaped opening of the two slit-shaped openings is arranged at an angle of 45° with respect to the longitudinal direction of the first slit-shaped opening, and wherein a cylinder J and an axis α are calculated according to:

$$J_0 = P_0 - M,$$
$$J_{45} = P_{45} - M,$$
$$J = \sqrt{J_0^2 + J_{45}^2}, \text{ and}$$
$$\alpha = \frac{1}{2}\tan^{-1}(J_{45}/J_0)$$

wherein $P_0$ is the optical power setting in Dioptres at maximum intensity for the first slit-shaped opening, $P_{45}$ is the optical power setting at maximum intensity for the second slit-shaped opening, and M is the optical power setting at maximum intensity for the third aperture.

Clause 31. The apparatus of any one of clauses 23 to 30, characterized in that the apparatus comprises separate light paths for each of the at least two apertures, and wherein the detector device (21A, 21B, 21C) comprises separate detectors for each of the at least two apertures.

Clause 32. The apparatus of any one of clauses 23 to 31, characterized in that the aperture device (19A, 19B, 19C) is configured to provide the at least two apertures as exchangeable apertures.

Clause 33. The apparatus of any one of clauses 23 to 32, characterized in that the aperture device (19A, 19B, 19C) is configured to provide the at least two apertures by rotating a slit-shaped opening.

Clause 34. The apparatus of any one of clauses 23 to 33, characterized in that the apparatus further comprises a visible light path separate from the aperture device (19A, 19B, 19C) and the detector device (21A, 21B, 21C).

Clause 35. The apparatus of clause 34, characterized by further comprising a stimulus (32) in the visible light path to be viewed by the eye (10).

Clause 36. The apparatus of clause 35, characterized in that the stimulus (32) comprises an eye chart.

Clause 37. The apparatus of any one of clauses 23 to 36, characterized by further comprising a scanning module (40) arranged at a conjugate pupil plane to a pupil of the eye (10) and configured to scan a visual field of the eye (10).

Clause 38. A method for determining a refractive error of an eye (10), comprising:
measuring an intensity of light coming from the eye (10) through each of at least two different apertures of an aperture device (19A, 19B, 19C),
characterized in that
the method further comprises determining the refractive error based on the intensities for each of the at least two different apertures,
wherein the different apertures comprise a first aperture with a first slit-shaped opening having a longitudinal direction of the slit in a horizontal direction with respect to the eye (10) and a second aperture with a second slit-shaped opening which is arranged at an angle of 45° with respect to the longitudinal direction of the first slit-shaped opening.

Clause 39. A method for determining a refractive error of an eye (10), comprising:
measuring an intensity of light coming from the eye (10) through each of at least two different apertures of an aperture device (19A, 19B, 19C),
characterized in that
the method further comprises determining the refractive error based on the intensities for each of the at least two different apertures, wherein the different apertures comprise a first aperture with a first slit-shaped opening and a second aperture with a second slit-shaped opening, and wherein the detector device (21A, 21B, 21C) is circular shaped with a diameter smaller than the different apertures.

Clause 40. The method of clause 38 or 39, characterized in that determining the refractive error is based on intensities for the at least two different apertures and a provided cylinder axis.

Clause 41. The method of clause 38 or 39, characterized in that determining the refractive error based on intensities for each of at least three different apertures.

Clause 42. The method of any one of clauses 38 to 41, characterized by further comprising at least one of:

varying an optical power of a light path from the eye (10) to a detector device (21A, 21B, 21C) for the detecting through a measurement range, or computationally varying an optical power of a light path from the eye (10) to the detector device (21A, 21B, 21C) through a measurement range, and by determining optical power settings at a maximum intensity for each of the at least two apertures, and determining the refractive error based on the optical power settings at maximum intensity.

Clause 43. The method of any one of clauses 38 to 42, characterized in that the two slit-shaped openings are arranged in different directions.

Clause 44. The method of any one of clauses 38 to 43, characterized in that the at least two apertures comprise a third aperture with a circular opening, the method further comprising determining a sphere of the refractive error based on the optical power setting at maximum intensity for the third aperture.

Clause 45. The method of any one of clauses 38 to 44, characterized in that the first slit-shaped opening has a longitudinal direction of the slit in a horizontal direction with respect to the eye (10), the second slit-shaped opening is arranged at an angle of 45° with respect to the longitudinal direction of the slit-shaped opening of the first slit-shaped opening, and wherein a cylinder J and an axis α are calculated according to:

$$J_0 = P_0 - M,$$
$$J_{45} = P_{45} - M,$$
$$J = \sqrt{J_0^2 + J_{45}^2}, \text{ and}$$
$$\alpha = \frac{1}{2}\tan^{-1}(J_{45}/J_0),$$

wherein $P_0$ is the optical power setting in Dioptres at maximum intensity for the first slit-shaped opening, $P_{45}$ is the optical power setting at maximum intensity for the second slit-shaped opening, and M is the optical power setting at maximum intensity for the third aperture.

Clause 46. The method of any one of clauses 38 to 45, characterized by further comprising providing a stimulus (32) in a visible light path to be viewed by the eye (10).

Clause 47. The method of any one of clauses 38 to 46, characterized by further comprising scanning a visual field of the eye (10).

Clause 48. A method for producing a lens for spectacle glasses, characterized by comprising:

determining the refractive error of an eye (10) according to the method of any one of clauses 38 to 47, and producing the lens based on the determined refractive error.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An apparatus for determining a refractive error of an eye, the apparatus comprising:

an illumination device;

an aperture device configured to provide at least three different apertures and configured to receive light coming from the eye through the at least three different apertures of the aperture device; and a detector device configured to measure an intensity of the light coming from the eye through each of the at least three different apertures of the aperture device, wherein the at least three different apertures are provided in at least three different locations simultaneously and include a first aperture with a first slit-shaped opening having a longitudinal direction of the slit in a horizontal direction with respect to the eye, a second aperture with a second slit-shaped opening being arranged at an angle of 45° with respect to the longitudinal direction of the first slit-shaped opening, and a third aperture with a circular opening, and wherein the detector device includes separate detectors for each of the at least three different apertures.

2. An apparatus for determining a refractive error of an eye, the apparatus comprising:

an illumination device;

an aperture device configured to provide at least two different apertures and configured to receive light coming from the eye through the at least two different apertures of the aperture device; and a detector device configured to measure an intensity of the light coming from the eye through each of the different apertures of the aperture device, wherein the at least two different apertures include a first aperture with a first slit-shaped opening and a second aperture with a second slit-shaped opening, and wherein the detector device is circular shaped with a diameter smaller than the at least two different apertures.

3. The apparatus of claim 2, wherein the first and second slit-shaped openings are arranged in different directions.

4. The apparatus of claim 2, wherein one of the at least two different apertures is a third aperture with a circular opening or a third aperture with a third slit-shaped opening.

5. The apparatus of claim 4, wherein the computing device is configured to determine a sphere of the refractive error based on optical power setting at maximum intensity for the third aperture with a circular opening.

6. The apparatus of claim 1, wherein the apparatus further comprises a computing device configured to determine the refractive error based on the intensities of light for the different apertures.

7. The apparatus of claim 1, wherein the apparatus further comprises a computing device configured to determine the refractive error based on the intensities of light for the different apertures and a cylinder axis provided to the computing device.

8. The apparatus of claim 1, further comprising at least one of:
- an optical power changing device, wherein the computing device is configured to control the optical power changing device to vary an optical power of a light path from the eye to the detector device through a measurement range; or
- the computing device being configured to computationally vary an optical power of a light path from the eye to the detector device through a measurement range, wherein the computing device is further configured to determine optical power settings at a maximum intensity for each of the different apertures, and to determine the refractive error based on the optical power settings at a maximum intensity.

9. The apparatus of claim 1, wherein the apparatus comprises separate light paths for each of the different apertures, and wherein the detector device includes separate detectors for each of the different apertures.

10. The apparatus of claim 1, wherein the aperture device is configured to provide the different apertures as exchangeable apertures.

11. The apparatus of claim 1, wherein the aperture device is configured to provide the different apertures by rotating of a slit-shaped opening.

12. The apparatus of claim 1, wherein the apparatus further comprises a visible light path separate from the aperture device and the detector device.

13. The apparatus of claim 12, further comprising a stimulus in the visible light path to be viewed by the eye.

14. The apparatus of claim 1, further comprising a scanning module arranged at a conjugate pupil plane to a pupil of the eye and configured to scan a visual field of the eye.

15. An apparatus for determining a refractive error of an eye, the apparatus comprising:
- an illumination device;
- an aperture device configured to provide at least three different apertures and configured to receive light coming from the eye through the at least three different apertures of the aperture device; and
- a detector device configured to measure an intensity of the light coming from the eye through each of the at least three different apertures of the aperture device,
- wherein the at least three different apertures are provided in at least three different locations simultaneously and include a first aperture with a first slit-shaped opening having a longitudinal direction of the slit in a horizontal direction with respect to the eye, a second aperture with a second slit-shaped opening being arranged at an angle of 45° with respect to the longitudinal direction of the first slit-shaped opening, and a third aperture with a circular opening, and wherein the detector device includes separate detectors for each of the at least three different apertures,
- wherein a cylinder J and an axis $\alpha$ are calculated according to:

$$J_0 = P_0 - M,$$
$$J_{45} = P_{45} - M,$$
$$J = \sqrt{J_0^2 + J_{45}^2}, \text{ and}$$
$$\alpha = \frac{1}{2}\tan^{-1}(J_{45}/J_0),$$

wherein $P_0$ is the optical power setting in Dioptres at a maximum intensity for the first aperture with a first slit-shaped opening, $P_{45}$ is the optical power setting at the maximum intensity for the second aperture with a second slit-shaped opening, and M is the optical power setting at the maximum intensity for the third aperture.

16. A method for determining a refractive error of an eye, the method comprising:
- measuring an intensity of light coming from the eye through each of at least three different apertures of an aperture device,
- wherein the method further comprises determining the refractive error based on the intensities for each of the at least three different apertures, wherein the at least three different apertures provided in at least three different locations simultaneously include a first aperture with a first slit-shaped opening having a longitudinal direction of the slit in a horizontal direction with respect to the eye, a second aperture with a second slit-shaped opening being arranged at an angle of 45° with respect to the longitudinal direction of the first slit-shaped opening, and a third aperture with a circular opening.

17. A method for producing a lens for spectacle glasses, the method comprising:
- determining the refractive error of an eye according to the method of claim 16; and
- producing the lens based on the determined refractive error.

18. A method for determining a refractive error of an eye, the method comprising:
- measuring an intensity of light coming from the eye through each of at least two different apertures of an aperture device,
- wherein the method further comprises determining the refractive error based on the intensities for each of the at least two different apertures,
- wherein the at least two different apertures include a first aperture with a first slit-shaped opening and a second aperture with a second slit-shaped opening, and
- wherein the detector device is circular shaped with a diameter smaller than the at least two different apertures.

* * * * *

UNITED STATES PATENT AND TRADEMARK OFFICE
CERTIFICATE OF CORRECTION

PATENT NO. : 11,849,997 B2  
APPLICATION NO. : 18/181671  
DATED : December 26, 2023  
INVENTOR(S) : Nikolai Suchkov, Alexander Leube and Siegfried Wahl Page 1 of 1

It is certified that error appears in the above-identified patent and that said Letters Patent is hereby corrected as shown below:

In the Specification

In Column 5, Line 64: change "Homer" to -- Horner --

In Column 10, Line 22: change "$P_O$" to -- $P_0$ --

In Column 10, Line 26: change "axis a" to -- axis $\alpha$ --

Signed and Sealed this  
Thirtieth Day of January, 2024

Katherine Kelly Vidal  
*Director of the United States Patent and Trademark Office*